United States Patent
Wang et al.

(10) Patent No.: US 9,192,770 B2
(45) Date of Patent: Nov. 24, 2015

(54) MEDICAL DEVICE COMMUNICATION SYSTEM AND METHOD

(71) Applicant: Medtronic, Inc., Minneapolis, MN (US)

(72) Inventors: Yu Wang, Plymouth, MN (US); George C. Rosar, Minneapolis, MN (US); Nicholas C. Wine, Minneapolis, MN (US); Gregory Haubrich, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 459 days.

(21) Appl. No.: 13/665,076

(22) Filed: Oct. 31, 2012

(65) Prior Publication Data

US 2014/0121727 A1    May 1, 2014

(51) Int. Cl.
   H04B 7/00      (2006.01)
   H04B 1/06      (2006.01)
   H04B 1/16      (2006.01)
   A61N 1/372     (2006.01)
   H04W 52/02     (2009.01)

(52) U.S. Cl.
   CPC ........ *A61N 1/37223* (2013.01); *A61N 1/37276* (2013.01); *H04W 52/0229* (2013.01)

(58) Field of Classification Search
   CPC ....... H03D 11/00; H03D 11/02; H03B 25/00; H04W 52/0029
   USPC ............... 455/41.1–41.3, 214–215, 334, 336, 455/343.2, 255–260, 313, 318
   See application file for complete search history.

(56) References Cited

U.S. PATENT DOCUMENTS

| | | | |
|---|---|---|---|
| 5,630,216 A | 5/1997 | McEwan | |
| 6,201,993 B1 | 3/2001 | Kruse | |
| 6,487,264 B1 * | 11/2002 | Alley et al. | 375/361 |
| 6,904,101 B1 | 6/2005 | Tang | |
| 7,215,936 B2 * | 5/2007 | Sadowski | 455/215 |
| 7,263,138 B2 | 8/2007 | Lourens | |
| 7,664,553 B2 | 2/2010 | Roberts | |
| 7,890,181 B2 | 2/2011 | Denzene | |
| 8,232,868 B2 * | 7/2012 | Steeves | 340/10.4 |
| 8,761,307 B1 * | 6/2014 | Ionescu et al. | 375/316 |
| 8,842,792 B2 * | 9/2014 | Jantunen et al. | 375/356 |
| 8,947,171 B1 * | 2/2015 | Mohanty | 331/116 M |
| 2005/0069051 A1 * | 3/2005 | Lourens | 375/316 |
| 2005/0255820 A1 * | 11/2005 | Ruhm et al. | 455/313 |
| 2005/0283207 A1 | 12/2005 | Hochmair et al. | |
| 2007/0060976 A1 | 3/2007 | Denzene et al. | |
| 2007/0139130 A1 * | 6/2007 | Kim et al. | 331/185 |
| 2007/0153705 A1 | 7/2007 | Rosar | |

(Continued)

FOREIGN PATENT DOCUMENTS

| EP | 1766882 A2 | 2/2006 |
|---|---|---|
| EP | 2222124 A1 | 8/2010 |

(Continued)

*Primary Examiner* — Simon Nguyen
(74) *Attorney, Agent, or Firm* — Michael J. Ostrom

(57) ABSTRACT

An implantable medical device is provided having circuitry to control operation of the implantable medical device and a receiver configured to receive communication signals on an allocated band of a plurality of communication channels separated in frequency by a channel spacing. The receiver includes an oscillator and a signal source configured to apply a quench signal to the oscillator. The quench signal has a frequency corresponding to the channel spacing. The receiver is enabled to receive on all of the plurality of communication channels simultaneously by applying the quench signal.

26 Claims, 8 Drawing Sheets

(56) References Cited

U.S. PATENT DOCUMENTS

| | | | |
|---|---|---|---|
| 2008/0136473 A1* | 6/2008 | Bollenbeck et al. | 327/156 |
| 2008/0154342 A1 | 6/2008 | Digby et al. | |
| 2009/0252042 A1 | 10/2009 | Bradley | |
| 2009/0305628 A1* | 12/2009 | Vavik | 455/14 |
| 2012/0307839 A1* | 12/2012 | Ionescu et al. | 370/431 |
| 2014/0027638 A1* | 1/2014 | Chang et al. | 250/338.1 |

FOREIGN PATENT DOCUMENTS

| | | |
|---|---|---|
| WO | 03/101536 A1 | 12/2003 |
| WO | 2005104006 A3 | 3/2005 |
| WO | 2005109351 A1 | 11/2005 |
| WO | 2006116004 | 2/2006 |

\* cited by examiner

MEDICAL DEVICE COMMUNICATION SYSTEM AND METHOD

FIELD OF THE DISCLOSURE

The disclosure relates generally to wireless communication systems, and in particular, to a wireless communication system for use in a medical device system.

BACKGROUND

Medical device systems may use wireless communication for transmitting data from one device to another. For example, an implantable or external monitoring or therapy delivery device may receive programming commands or operational parameters from a programmer. The monitoring or therapy delivery device may transmit data to the programmer to enable a clinical or technical expert to review data acquired by the device.

Telemetry circuitry in an implantable medical device (IMD) is normally in a minimum power or OFF state, sometimes referred to as a "sleep" state. Since the implanted device does not know when an external device might be attempting to communicate with the implanted device, the receiving circuitry of an IMD is typically powered up periodically to enable the implanted circuitry to poll for a "wake-up" signal from an external device that may be sending one. If a wake-up signal is received, the telemetry circuitry is fully powered-up to enable bi-directional communication with the external device.

If no wake-up signal is received, the implanted receiver is powered down again, or put back into the sleep state. The receiver may be enabled to "listen" for a wake-up signal as often as once per second or fraction thereof. As such, considerable power is used to enable the receiver to listen for a wake-up signal even when no wake-up signal is actually received. Since it is desirable to flexibly establish communication with the implanted device at any time with a quick response time by the implanted device, it is desirable to enable frequent "listening" periods while minimizing the power requirements of the receiver each time it is powered-up for listening for a wake-up signal.

Generally, implantable medical devices have a limited size and therefore limited battery space and power capacity. By reducing the power consumed by the telemetry receiver when enabled to listen for a wake-up signal, the size of an implanted device can be reduced, the longevity of the implanted device can be increased, and/or the conserved power can be utilized for other functions performed by the device. External devices, for example wearable devices, may not have the same size limitations as implantable devices, but power conservation may still be a goal to allow a patient to be ambulatory without frequent battery changes or charges and allow flexible communication with another device without requiring patient intervention. Accordingly, a need remains for communication systems for use with medical device systems that reduce the power requirements for establishing a communication link between a patient monitoring or therapy delivery device and a programmer or other communication device while still enabling flexibility in the frequency and timing of establishing the communication link.

SUMMARY

A communication system for use with medical devices includes a receiver configured to receive communication signals on an allocated band of communication channels separated in frequency by a channel spacing and a transmitter configured to transmit a signal in the band. A control circuit is configured to enable the receiver to receive on all of the plurality of communication channels simultaneously and in response to receiving the transmitted signal select a channel for communication with the transmitter. In one embodiment the receiver includes a resonator coupled to an oscillator and a signal source controlled by the control circuit to apply a quench signal to the oscillator, the quench signal having a frequency corresponding to the channel spacing, the receiver being enabled to receive on all of the plurality of communication channels simultaneously by applying the quench signal. In various embodiments, a quench signal is applied to a receiver amplifier, a receiver detector, and/or an oscillator coupled to a resonator. The quench signal is applied to operate the detector and/or the amplifier on duty cycle basis and/or to the oscillator to control the receiver to be enabled to receive on all channels within one or more channel bands simultaneously.

In one example, this disclosure provides an implantable medical device having circuitry to control operation of the implantable medical device and a receiver configured to receive communication signals on an allocated band of a plurality of communication channels separated in frequency by a channel spacing. The receiver includes an oscillator and a signal source configured to apply a quench signal to the oscillator. The quench signal has a frequency corresponding to the channel spacing. The receiver is enabled to receive on all of the plurality of communication channels simultaneously by applying the quench signal.

In another example, this disclosure provides a method of operating a receiver configured to receive communication signals on an allocated band of a plurality of communication channels separated in frequency by a channel spacing. The method includes generating a quench signal having a frequency corresponding to the channel spacing and applying the quench signal to an oscillator of the receiver to enable the receiver to receive communication signals in the allocated band to receive on all of the plurality of communication channels simultaneously.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

In the following description, references are made to illustrative embodiments. It is understood that other embodiments may be utilized without departing from the scope of the disclosure.

Figure 1:
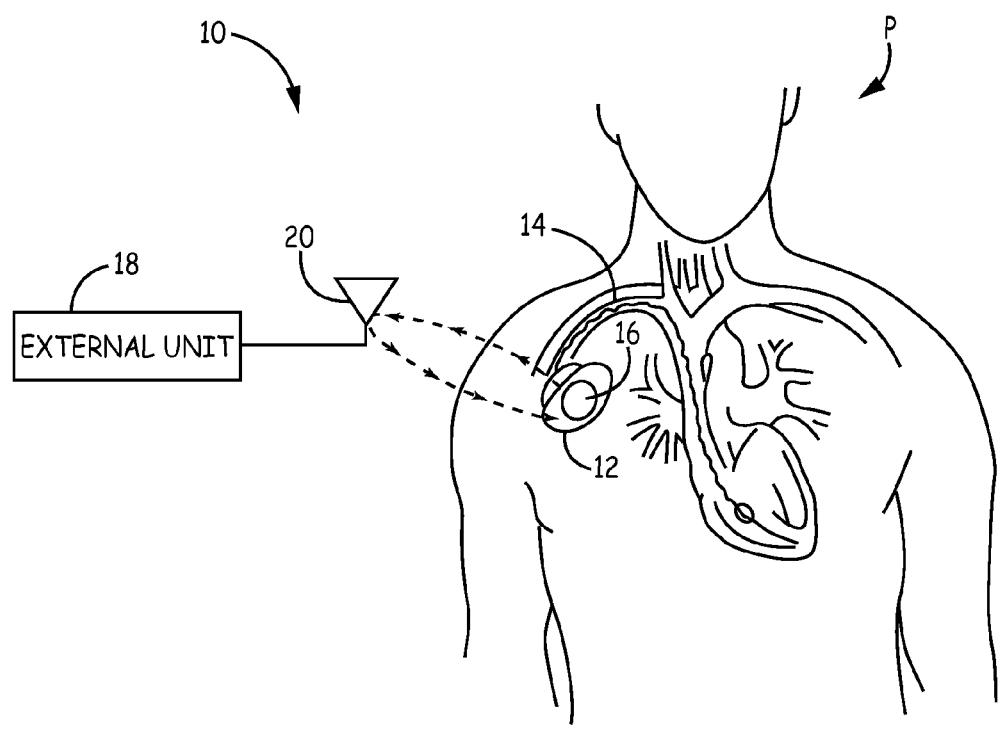
FIG. 1 is a schematic diagram illustrating a communication system according to one embodiment.

FIG. 1 is a schematic diagram illustrating a communication system 10 that enables communication between an IMD 12 and external unit 18. In one embodiment, IMD 12 is an implantable cardiac electrical stimulation device such as a cardiac pacemaker or implantable cardioverter defibrillator (ICD), but the disclosed communication system is equally applicable to many types of implantable medical devices, including implantable monitors, drug delivery devices, neurostimulation devices and more, and may even be applicable to external medical devices. IMD 12 is capable of providing cardiac electrical stimulation therapies and/or sensing physiological events of the heart of patient P via cardiac lead(s) 14. Antenna 16 is used to communicate with external unit 18 and may be any device capable of sending or receiving electromagnetic energy, including, for example, a surface mounted antenna, an inductor, or a half-wave strip. Antenna 16 may be incorporated in or along an IMD housing or lead connector block in various embodiments.

External unit 18 is a device, such as a medical device programmer, capable of communication with IMD 12 via external antenna 20. External unit 18 includes antenna 20, which may be any type of RF antenna capable of communicating in the desired RF frequencies with IMD 12, and may be located inside or outside of a housing of external unit 18. External unit 18 may be embodied as a programmer used in a clinic or hospital, for example, for programming operational parameters and or operating programs in IMD 12 for controlling IMD function and for interrogating IMD 12 for retrieving data accumulated by IMD 12. For example, upon an interrogation command transmitted from external unit 18 to IMD 12, operational device-related data, therapy delivery data, and/or physiological signal data stored by IMD 12 may be transmitted from IMD 12 to external unit 18. In alternative embodiments, external unit 18 may be a handheld device, a home monitor, a computer or any other device enabled for wireless telemetric communication with IMD 10 and used by a patient, clinician or other caregiver.

Figure 2:
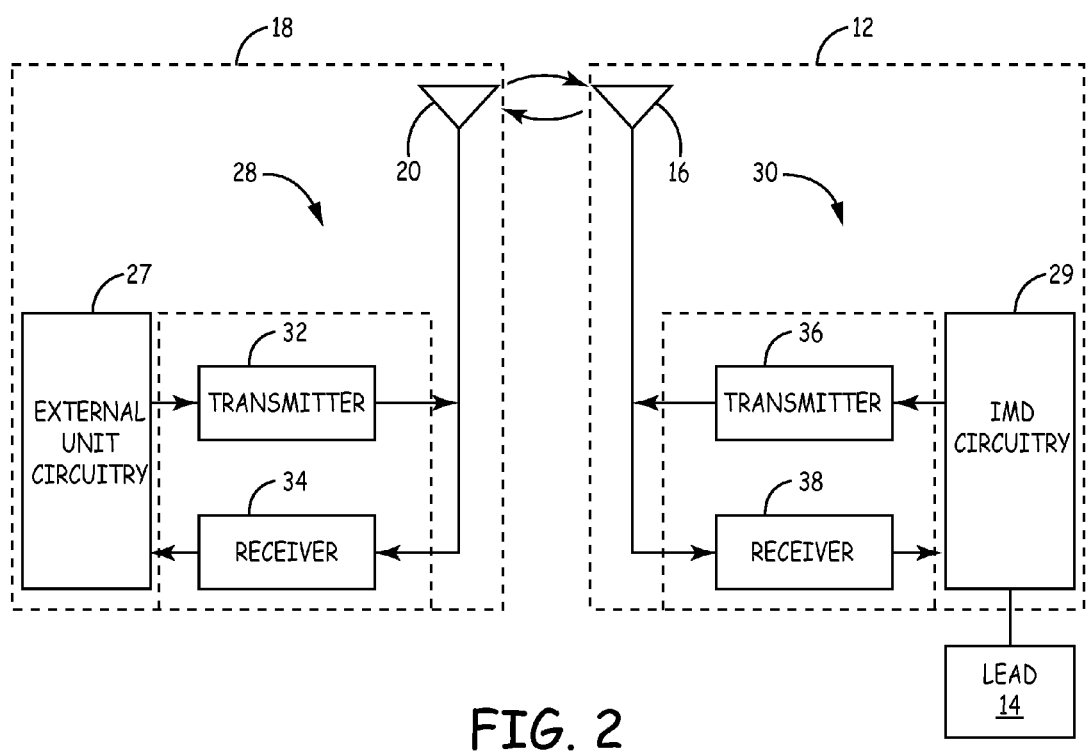
FIG. 2 is a block diagram illustrating some of the components of an IMD and an external unit that make up the communication system shown in FIG. 1.

FIG. 2 is a block diagram illustrating some of the components of IMD 12 and external unit 18 that make up communication system 10. External unit 18 includes antenna 20, external unit circuitry 27, and transceiver 28. Antenna 20 is coupled to transceiver 28 of external unit 18. External unit circuitry 27 includes a microcomputer and software to control the operation of external unit 18. Transceiver 28 enables external unit circuitry 27 to transmit and receive communications with IMD 12. Transceiver 28 of external unit 18 includes transmitter 32 and receiver 34.

IMD circuitry 29 includes a microprocessor for controlling the operation of IMD 12 and for processing data, therapy delivery circuitry for delivering a therapy through lead 14, and sensors for generating data, including data generated by detecting electrical signals on lead 14. Transceiver 30, coupled to antenna 16, enables IMD circuitry 29 to transmit and receive communications with external unit 18. Transceiver 30 includes transmitter 36 and receiver 38, which transmit and receive data using RF electromagnetic waves.

Communication between IMD 12 and external unit 18 can be performed over any communication band. In one embodiment, the communication occurs over a public radio frequency band. In another embodiment, the communication occurs over the Medical Implant Communication (MICs) band between 402 MHz and 405 MHz. In another embodiment, the communication occurs over the Medical Data Services (MEDS) band, which is a split band having an upper MEDS band (405-406 MHz) and a lower MEDS band (401-402 MHz). Although the techniques disclosed herein are described with reference to illustrative radio frequency bands, it is recognized that the disclosed techniques may be implemented in conjunction with any communication bands and may be useful with other types of electromagnetic communication.

Because IMD 12 has a finite battery capacity, one consideration in the design of RF communication system 10 is the energy efficiency of IMD 12. One factor in the energy efficiency of IMD 12 is the time transceiver 30 is engaged in actively transmitting or receiving. Thus, an improvement in energy efficiency of transceiver 30 will lead to increased battery life of IMD 12. Energy efficiency is less of an issue in the design of external unit 18, because external unit 18 may not be restricted to the same size limitations and can therefore dedicate a larger volume for battery(ies) or could be connected to an external power source such as a 120V AC. Therefore, reducing the energy consumption of transceiver 30 is particularly beneficial. It is contemplated, however, that a power efficient receiver and associated techniques as described herein may be implemented in one or both medical devices being used in a two-way communication system 10, such as both of devices 12 and 18.

While transmitters only need to be turned on when there is data to transmit, receivers are turned on much more frequently. No communication can take place unless the receiver is on, at least momentarily, to detect an attempted transmission from a transmitter. To provide a fast response time, a receiver may be periodically turned on to "listen" for a wake up signal from a transmitter. In other words, the receiver may be duty cycled between a minimum power or OFF state (referred to herein as a "sleep" state) and the listen state during which the receiver is powered on to listen for the wake up signal. The receiver may be periodically turned on to listen for the wake up signal as often as once or twice every second or more. Therefore, an increase in the energy efficiency of a receiver can provide a significant increase in the effective life of the power supply of the medical device.

Returning to communication system 10 of FIG. 2, transmitter 32 may transmit a wake-up signal prior to the transmission of data. Receiver 38 periodically powers up to enable receiver to listen for this wake up signal, rather than remaining on at all times, while still ensuring that receiver 38 will not miss the transmission of any data. The wake-up signal contains a modulation pattern recognizable by receiver 38. If receiver 38 does not detect any signal on the communication band or detects signals on the communication band, but finds that the signals do not contain the recognizable modulation pattern, receiver 38 can shut down since the detected signal is not a communication initiated by transmitter 32 for receiver 38. Furthermore, the wake-up signal may contain embedded data that allows the receiver 38 to identify an intended communication channel for subsequent transmission of data. Receiver 38 may continue operating in a low power receiver mode while receiving the embedded data, and then adjust its receiver configuration settings as specified by the embedded data to initiate the higher power receiver mode for receipt and analysis of the transmitted data on the communication channel identified in the wake-up signal.

Receiver 38 of IMD 12 operates in a low-power mode that can simultaneously sample for energy on a plurality of communication channels (and in some instances all of the communication channels) in an allocated communication band utilized by the receiver. The receiver then operates in a high power communication mode for receiving data communication on a single channel within the communication band in response to detecting a wake-up signal. Each of transceivers 28 and 30 may include control circuitry which initiate and control operations performed by the transmitters 32, 36 and receivers 34, 38, respectively. Transceiver control circuitry may alternatively be implemented, all or in part, in external unit circuitry 27 and IMD circuitry 29 for respectively controlling the operating mode of transceivers 28 and 30. Control circuitry may include digital processing circuitry, state machines, logic circuitry or other circuitry implemented to control the operation of a receiver as described herein.

Figure 3:
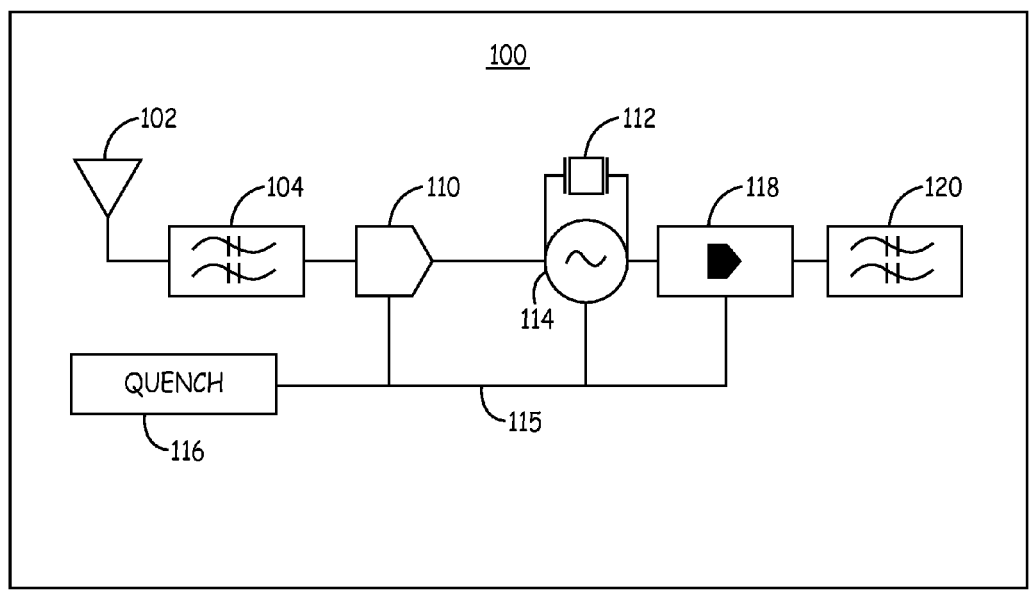
FIG. 3 is a block diagram of a medical device receiver according to one embodiment.

FIG. 3 is a block diagram of a medical device receiver 100 according to one embodiment. Receiver 38 and optionally receiver 34 shown in FIG. 2 may correspond to receiver 100, which is configured as a power efficient receiver for sampling a plurality of available channels and, in some instances, all of the available channels in an intended communication band simultaneously during a low power wake-up mode. In an illustrative embodiment, receiver 100 includes a number of components that for a receive path of receiver 100, including a preamplifier 102, an input filter 104, a low noise amplifier (LNA) 110, a resonator 112 coupled to an oscillator 114, a detector 118 and a channel filter 120. Resonator 112 may be a high quality factor (Q) resonator. Resonator 112 may be implemented as a surface acoustic wave (SAW) resonator, a bulk acoustic wave (BAW) resonator, a microelectromechanical systems (MEMS) resonator, a film bulk acoustic resonator (FBAR), or a selectable bank of high Q resonators in some examples. Resonator 112 is used as a stable reference for receiver 100 and provides improved selectivity based on the high Q. For example, resonator 112 may be provided with a Q factor of at least 1000. The high Q resonator 112 may be provided having a resonance frequency bandwidth corresponding to, e.g. approximately equal to, a frequency bandwidth of a single channel of an allocated band of communication channels to provide channel selectivity.

A quench frequency signal source 116, e.g. provided as an oscillator, is controlled by the receiver control circuitry to produce a quench signal that is applied at least one of LNA 110, oscillator 114 and detector 118. In embodiments where the quench frequency signal is applied to oscillator 114, the receiver may operate as a super regenerative receiver (SRR). However in other embodiments, the quench frequency signal may be applied to one or more other components within the receive path of receiver 100 in addition to or instead of oscillator 114. For example, the quench frequency signal may be applied to LNA 110 and/or detector 118. By applying the quench signal from source 116 to oscillator 114, all receiving channels in a communication band are enabled simultaneously to receive a transmitted input signal. By applying the quench signal to LNA 110 and/or detector 118, current consumption by receiver 100 is reduced. LNA 110 is optional in some embodiments in which case the quench signal 115 is provided to oscillator 114 and/or detector 118.

A SRR is generally a low cost component but typically has multiple mixing products considered to be a disadvantage in medical device communication systems because of undesired signals that result and consequential limitations on the communication bandwidth of SRRs. Receiver 100, however, may be provided with a resonator 112 having a center frequency within the bandwidth of the range of allocated communication channels. For example, resonator 112 may have a center frequency corresponding to the center of a band of communication channels used by receiver 100. The oscillator 114 may be quenched with a quench frequency from source 116 equal to a channel spacing of the band of communication channels. The resultant mixing products of the receiver 100 will fall on every channel in the band, one mixing product on each channel. In this way, the receiver 100 is enabled to receive signals on all channels in the communication band simultaneously with a single quench frequency applied to oscillator 114. In other embodiments, the quench frequency from source 116 may be equal to a multiple of the channel spacing (e.g., double the channel spacing) such that receiver 100 is enable to receive on a plurality of channels in the communication band simultaneously, but not all of the communication channels.

In an illustrative example, if receiver 100 utilizes the MEDS band, resonator 112 is provided with a center frequency centered in the frequency range of the MEDS band, e.g. either the upper MEDS band (405-406 MHz) or the lower MEDS band (401-402 MHz). For example, in one embodiment for operation in the lower MEDS band, resonator 112 is provided with a center frequency of 401.5 and a quench signal of 100 kHz is applied to the oscillator 114 resulting in 9 equally spaced channels (401.1, 401.2, 401.3, ... 401.9) that are available for receiving communication signals simultaneously. Other communication bands and quench frequencies can be used to obtain n equally spaced channels, separated by a channel spacing used to define the quench frequency signal applied to the oscillator 114, and enabled to simultaneously receive transmission signals. In other examples, the resonator 112 may be provided with a center frequency corresponding to any channel in the communication band and is not required to be aligned with the center frequency of the selected frequency band. The resonator center frequency may be along an edge of the channel band.

In alternative embodiments, resonator 112 may be provided having a center frequency outside an allocated band of communication channels. The center frequency of resonator 112 may be below the lowest frequency channel of the band or above the highest frequency channel of the band. The LNA 110, oscillator 114 and/or detector 118 may be quenched with a signal frequency corresponding to the channel spacing. In such embodiments, some mixing components of the receiver 100 will fall within the band and some outside the band. However, by adjusting the quench signal source 116 to provide a quench signal corresponding to an intended communication channel, channel selectivity can be improved. Using the example of the lower MEDS band again, if the resonator 112 is provided with a center frequency of 391.1 MHz, and a quench signal of 10 MHZ is applied, the 401.1 MHz channel can be selected. If a quench signal is adjusted to 10.1 MHz, the 401.2 MHz channel can be selected. If a quench signal is adjusted to 10.2 MHz, the 401.3 MHz channel can be selected, and so on. Accordingly, by implementing resonator 112 with an off-band center frequency, improved channel selectivity can be achieved through adjustment of the quench frequency signal 115 to tune the receiver to a desired communication channel during a communication session. The quench signal source 116 may provide a single quench signal 115 corresponding to a channel spacing. Alternatively, quench signal source 116 may provide one or more signals 115 having frequency(ies) that achieve the desired mixing frequencies across a channel band.

In various embodiments, the quench signal 115 produced by source 116 is applied to LNA 110, oscillator 114, detector 118 or any combination thereof. Application of a selected quench frequency to oscillator 114 equal to the channel spacing of an allocated band of communication channels or another frequency that achieves the desired mixing frequencies corresponding to the channel frequencies enables receiver 100 to receive on all or at least a plurality of the communication channels simultaneously. Application of the quench signal 115 to the LNA 110 and/or detector 118 reduces current consumption by the receiver 100. By applying the quench signal to LNA 110 and detector 118, the LNA 110 and detector 118 are operated on a duty cycle rather than continuous basis, reducing current consumption during the polling period. By applying the same quench signal 115 to oscillator 114 and to LNA 110 and detector 118, the LNA 110 and detector 118 are duty cycled at the same rate oscillator 114 is quenched to conserve current without input signal data loss. In this way, receiver 100 can listen for a wake-up signal on all channels of an allocated channel band simultaneously and go back to sleep if no wake-up signal is received using very low current. All channels are available simultaneously for detection of any signals in the channel band.

Detector 118 is configured for receiving and demodulating signals from all channels in the allocated channel band, including, for example, FSK (frequency shift keyed), ASK (amplitude shift keyed), and/or OOK (on/off keyed) data signals. A front end filter 104 may optionally be provided as a tunable filter for selectively choosing a designated channel frequency for establishing a communication link with a transmitting device. In an alternative embodiment, channel filter 120 is provided as an adjustable filter for selecting a channel for communicating with the transmitting device. In still other embodiments, the quench signal source 116 is adjusted to provide a quench signal 115 applied to oscillator 114 that results in channel selection for receiving transmission signals on a designated channel during a communication session.

Figure 4:
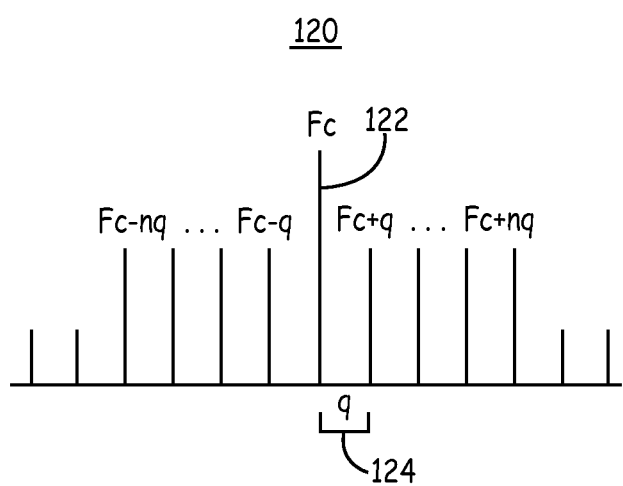
FIG. 4 is an illustrative plot of channel frequencies available for simultaneously receiving transmitted data in the receiver of FIG. 3.

FIG. 4 is an illustrative plot 120 of channel frequencies available for simultaneously receiving transmitted data in receiver 100. Fc 122 is a center frequency of resonator 112 in one embodiment. A quench frequency (q) 124 is applied to oscillator 114 resulting in mixing frequencies aligned with 2n+1 equally spaced channels ranging from Fc−nq to Fc+nq. Any one of the desired channels Fc−nq to Fc+nq may be selected with the use of an adjustable channel selection, e.g. implemented as an adjustable bandpass front end filter 104, channel filter 120, or by adjusting the quench signal 115 applied by source 116 in FIG. 3. One channel will be passed as output from receiver 100 and the other channels will be rejected.

In another embodiment, front end filter 104 may be implemented as a roofing filter used to attenuate frequencies outside an allocated channel band, e.g. below Fc−nq and above Fc+nq in the illustrative plot 120. All channels Fc−nq through Fc+nq can simultaneously receive a transmitted signal, and all channels are demodulated by detector 118 at the same time. A single quench frequency may be applied to oscillator 114 and optionally to LNA 110 and/or detector 118 during a periodic low-power "listening" mode. If no wake-up signal is received during the listening period on any of the channels Fc−nq through Fc+nq, the receiver is again powered down (i.e. put to sleep).

In one embodiment, if a wake-up signal is received during a listening period, channel selection, which may be implemented as an adjustable bandpass input filter 104 or an adjustable bandpass channel filter 120, could be enabled to pass each channel signal to the IMD circuitry 29 individually. The signal energy for each channel could then be measured to determine which channel should be selected for full communication. Alternatively, the quench signal 115 provided by source 116 may be adjusted to provide single channel selectivity, one channel at a time, to determine which channel is the intended communication channel. The other channels can be rejected and the selected channel signal passed by the channel filter 120 to the IMD circuitry 29.

In this way, power is saved compared to a scanning receiver that first scans all channels for receiving a wake-up signal. In a scanning receiver, all channels are scanned, typically one at a time, during a listening period to determine if a wake-up signal is being transmitted on any of the channel bands. A required amount of power is consumed to scan through all the channels even when no wake-up signal is received. When all channels are receiving simultaneously in receiver 100, a wake-up signal can be detected using less power than required to scan through the individual channels. If no wake-up signal is received, all channels are put back to sleep. In this way, receiver 100, enabled to simultaneously receive on all channels by application of a single quench frequency signal, uses less power than a scanning receiver when no wake-up signal is received during a listening period. The listening period can be much shorter when all channels receive simultaneously than when each channel is scanned individually for a wake-up signal.

Figure 5:
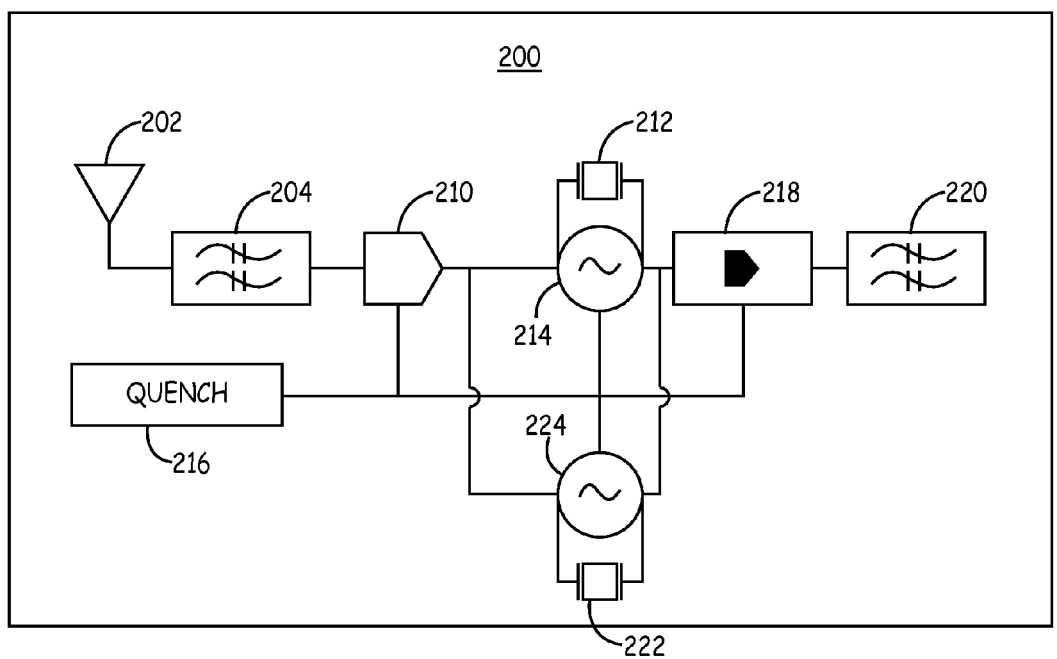
FIG. 5 is a block diagram of a medical device receiver according to an alternative embodiment.

FIG. 5 is a block diagram of a medical device receiver 200 according to an alternative embodiment. Receiver 200 includes a pre-amplifier 202, an input filter 204, LNA 210, first resonator 212 coupled to oscillator 214, detector 218 and channel filter 220 as described above. Additionally, receiver 200 includes a second resonator 222 having a center frequency different than resonator 112 coupled to a second oscillator 224. For example, resonator 222 may be provided with a center frequency of 405.5 MHz corresponding to the center of the upper MEDS band of 405 MHz to 406 MHz. A quench signal of 100 kHz applied to oscillator 224 will result in a second set of 9 equally spaced channels (405.1 through 405.9) that can be used for communication. In addition to the 9 channels provided by resonator 212, a total of 18 communication channels are made available for simultaneous reception using a single quench frequency signal 215 from source 216. It is should be understood that the example of 9 equally spaced channels per band for a total of 18 channels is merely illustrative and that the number of channels per band and the number of bands may vary between embodiments and such that a total number of channels may be less than or significantly more the 18 channels described in the foregoing example.

The diagram of FIG. 5 illustrates that multiple resonators can be used in the receiver with the same quench signal applied to the oscillators respectively coupled to each resonator to provide multiple, equally spaced communication channels enabled to receive simultaneously across a relatively broad communication bandwidth or multiple communication bandwidths. It is further recognized that in a receiver 200 including multiple resonators 212 and 222, the quench signal may be applied to LNA 210 and/or detector 218.

In the illustrative example discussed above, both resonators 212 and 222 are provided with a center frequency corresponding to a center channel of a respective channel band. In alternative embodiments, the center frequency of resonator 212 may be above, below or in a first channel band, e.g. the lower MEDS band, and the center frequency of resonator 222 may be above, below or in a second channel band, e.g. the upper MEDS band. A single quench frequency corresponding to the channel spacing of both bands may be applied to oscillators 214 and 224 to enable receiver 200 to receive on all channels in both channel bands simultaneously. The quench frequency (or a channel filter, e.g. 218) may then be adjusted in response to detecting a wake-up signal on any channel to select a single channel in one of the channel bands for receiving transmitted signals in a communication session.

In a receiver 200 including multiple resonators having center frequencies corresponding to a respective number of communication channel bands, a single oscillator 214 could be coupled to all resonators 212 and 222 rather than providing a dedicated oscillator for each resonator. Accordingly, a single oscillator 214 may be quenched by a single quench frequency 215 corresponding to a common channel spacing of multiple channel bands and coupled to multiple resonators, each resonator having a center frequency (in- or out-of-band) corresponding to a respective channel band.

Figure 6:
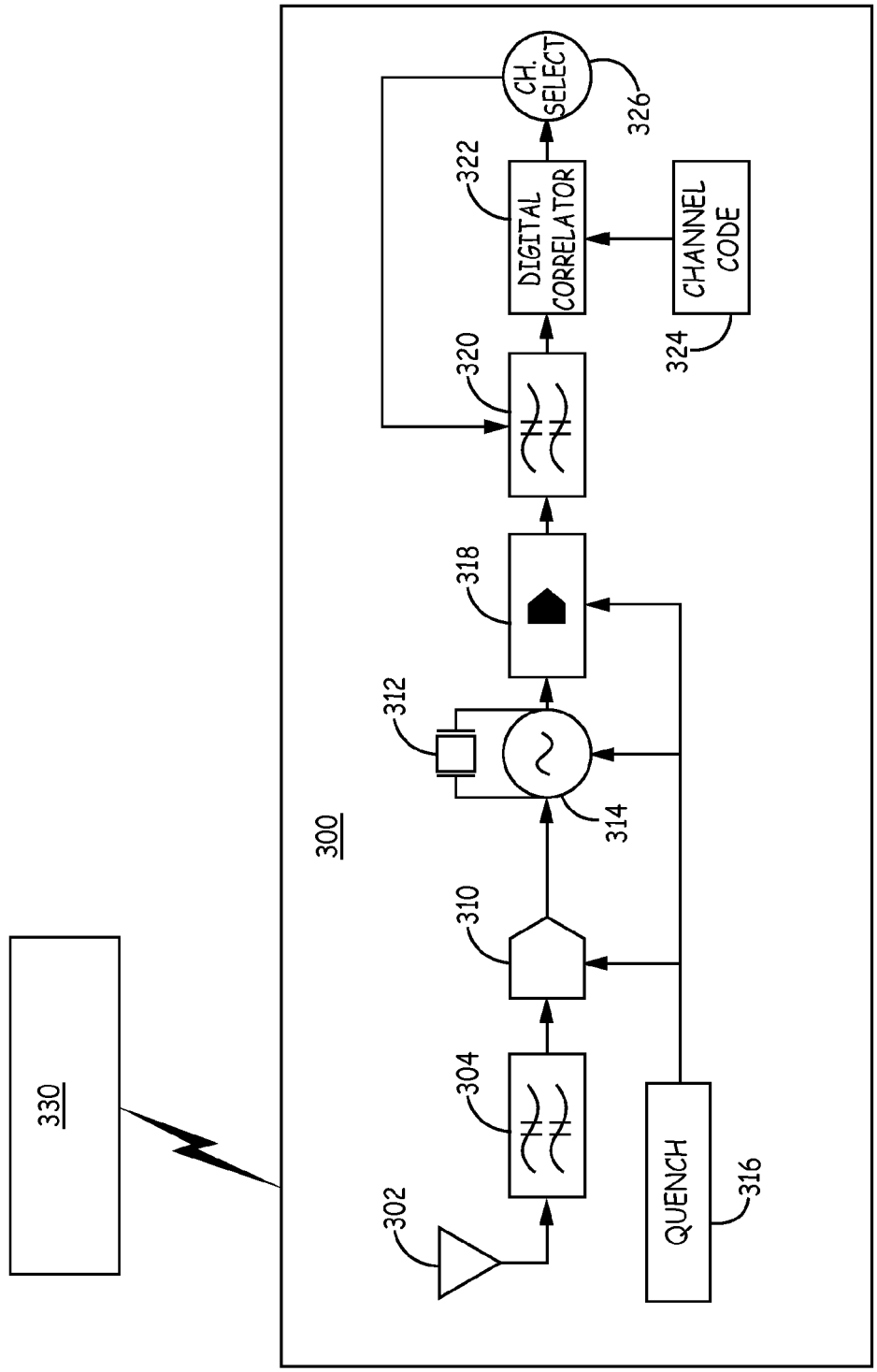
FIG. 6 is a functional block diagram of some components of a medical device communication system according to one embodiment.

FIG. 6 is a functional block diagram of some components of a medical device communication system according to one embodiment. Receiver 300 includes a pre-amplifier 302, an input filter 304, LNA 310, resonator 312 coupled to an oscillator 314, detector 318 and channel filter 320. As described previously, a quench signal source 316 provides a quench signal 315 to LNA 310, oscillator 314, and/or detector 318 to reduce current consumption. When signal 315 is applied to oscillator 314 at a frequency equal to the channel spacing of an allocated band of communication channels or other desired mixing frequency multiple, equally spaced channels are enabled to receive simultaneously by applying a single quench frequency as described above.

A transmitting device 330 transmits a signal on a selected one of the communication channels including a baseband signal code indicating the intended communication channel. The receiver 300 controls the quench signal source 316 to periodically apply quench signal 315 during a listening period, e.g. once or more per second, to enable reception on all channels simultaneously during the listening period. Detector 318 demodulates all channel signals.

A channel code 324 is stored in digital memory of receiver 300. Digital correlator 322 receives the demodulated detector signal and, using the stored channel code 324, identifies the intended communication channel by comparing the stored channel code 324 to the decoded baseband signal. The intended communication channel is identified by correlator 322 and indicated by an output channel select signal 326.

The output signal 326 identifying the intended communication channel is provided to channel filter 320, enabling and tuning channel filter 320 to pass the intended communication channel frequency. The intended communication channel is passed by channel filter 320 and remaining channels are rejected.

In this way, the coded baseband signal allows the intended communication channel to be identified by receiver 300 without having to scan each channel signal individually. Accordingly, a low-power receiver capable of simultaneously enabling 9, 18, 30 or any other number of channels in one or more allocated communication channel band(s) for detecting a wake-up signal is adapted to listen on all channels simultaneously then tune to a single channel for a full communication session. The receiver can be fully powered up in response to a detected wake-up signal occurring on any channel with the intended communication channel identified and selected by analysis of the decoded baseband signal of the wake-up signal without scanning through the available channels individually for detecting the wake-up signal or for identifying the intended communication channel once the wake-up signal is detected.

Figure 7:
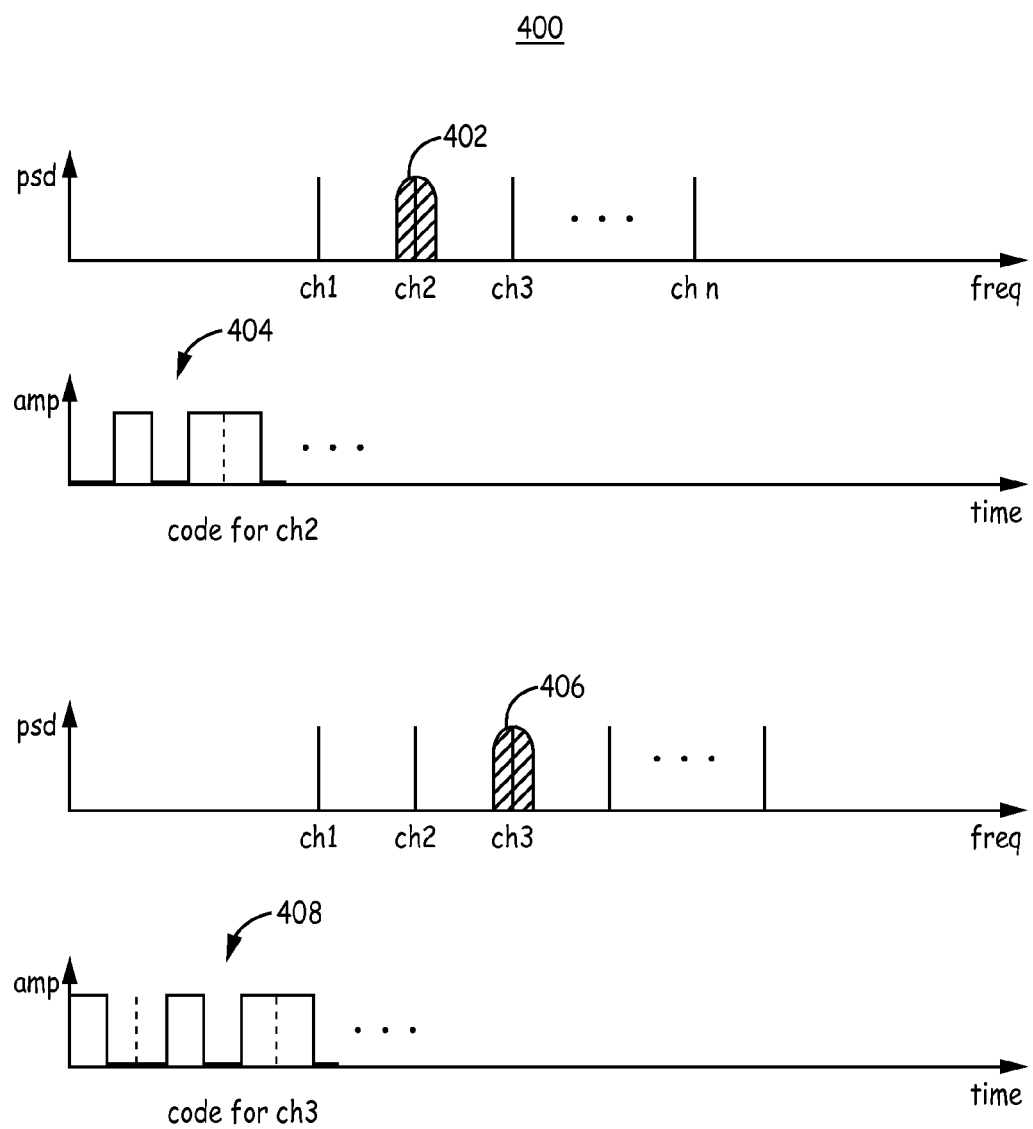
FIG. 7 is a plot of example channel codes that may be stored by a receiver and encoded in a baseline signal transmitted by a transmitting device.

FIG. 7 is a plot 400 of example channel codes that may be stored by receiver 300 and encoded in a baseline signal transmitted by a transmitting device 330. A signal centered on a channel frequency having a predetermined logic code specific for that channel is transmitted to identify the intended communication channel. For example, a baseband signal having a power spectral density (PSD) centered on a frequency 402 corresponding to channel 2 of a band of communication channels is transmitted with logic signal 404 to identify channel 2. A baseband signal having a PSD centered on a channel 3 frequency 406 and a channel-specific logic signal 408 identifies channel 3 as the intended communication channel.

The receiver 300 stores a unique coded sequence corresponding to each channel of the receiver 300 in the channel band. The coded sequence may be an amplitude, frequency, on/off or other modulated sequence. This coded sequence enables the receiver to receive on all channels simultaneously then select an intended channel for communication with transmitting device 330 according to the decoded baseband signal identified in a detected wake-up signal.

It is recognized that in a bi-directional communication system, transmitting device 330 may include a receiver circuit analogous to receiver 300 and receiver 300 may be included in a transceiver unit that includes a transmitter capable of transmitting signals to device 330.

Figure 8:
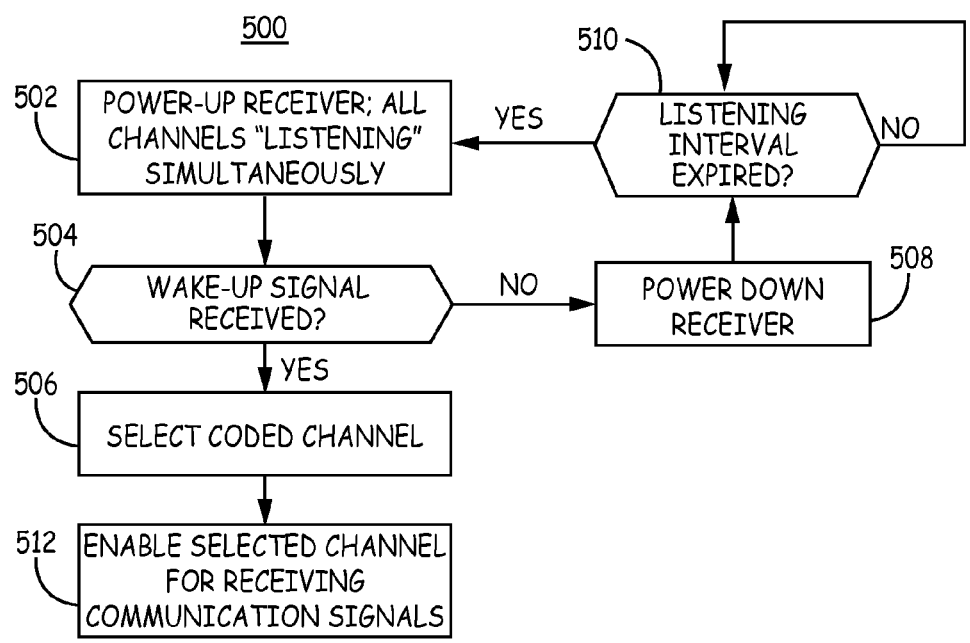
FIG. 8 is a flow chart of a method for waking up a receiver according to one embodiment.

FIG. 8 is a flow chart 500 of a method for operating a receiver according to one embodiment. At block 502, the receiver is powered up by control circuitry in a low-power "listening" mode by enabling a quench signal source, resonator(s) and associated oscillator(s). All channels are enabled to receive simultaneously by applying a quench frequency signal having a frequency corresponding to the channel spacing to the oscillator(s). If no wake-up signal is detected during a polling period on any channel at block 504, the receiver is powered down at block 508 and waits for a polling interval to expire at block 510. After expiration of the polling interval, which may be a fraction of a second, one second or a longer interval, the receiver is powered up again to enable the receiver to listen for a wake-up signal during a polling period on all receiver channels simultaneously at block 502.

If a wake-up signal is received on any channel, the receiver identifies an intended communication channel according to comparative analysis of a decoded baseband signal and channel codes stored in digital memory of transceiver 30 at block 506. The receiver is then fully powered up for signal reception on the selected channel at block 512. The quench signal and/or an adjustable channel selection filter are adjusted to tune the receiver to the selected channel. For example, at block 502, the receiver may be enabled to simultaneously receive on all channels in one or more channel bands by applying a single quench signal to one or more oscillators coupled to resonator(s) having a center frequency corresponding to each channel band. After identifying a selected communication channel at block 506, the quench signal is adjusted at block 512 to a difference between the resonator center frequency and the selected channel frequency to tune the receiver to the selected channel during a communication session. The quench signal may be applied to a LNA (if present) and the detector during both the polling period and during the full communication session for reducing current consumption.

The techniques described in this disclosure, including those attributed to the IMD or components of the IMD, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a non-transitory computer-readable medium such as RAM, ROM, NVRAM, EEPROM, or flash memory, magnetic data storage media, optical data storage media, or the like. The instructions may be executed to support one or more aspects of the functionality described in this disclosure.

A communication system and associated methods have been presented in the foregoing description with reference to specific embodiments. It is appreciated that various modifications to the referenced embodiments may be made without departing from the scope of the disclosure as set forth in the following claims.

The invention claimed is:

1. An implantable medical device comprising:
   circuitry to control operation of the implantable medical device; and
   a receiver configured to receive communication signals on an allocated band of a plurality of communication channels separated in frequency by a channel spacing, the receiver comprising:
   an oscillator; and
   a signal source configured to apply a quench signal to the oscillator, the quench signal having a frequency corresponding to the channel spacing, the receiver being enabled to receive on all of the plurality of communication channels simultaneously by applying the quench signal.

2. The implantable medical device of claim 1, wherein the receiver comprises at least one other component, wherein the signal source is configured to apply the quench signal to the at least one other component.

3. The implantable medical device of claim 2, wherein the at least one other component comprises a detector configured to demodulate the received communication signals, an amplifier configured to amplify the received communication signals, or both the detector and the amplifier.

4. The implantable medical device of claim 1, further comprising a resonator coupled to the oscillator.

5. The implantable medical device of claim 4, wherein the resonator has a resonance frequency bandwidth corresponding to a frequency bandwidth of one of the plurality of communication channels in the allocated band.

6. The implantable medical device of claim 4, wherein the resonator is a first resonator having a first center frequency;
   the allocated band of the plurality of communication channels comprises a first plurality of communication channels in a first band and a second plurality of communication channels in a second band different than the first band;
   the receiver further comprising a second resonator coupled to the oscillator, the second resonator having a second center frequency different than the first center frequency; and
   the receiver being enabled to receive on all of the first plurality of communication channels and all of the second plurality of communication channels simultaneously by applying the quench signal to the oscillator.

7. The implantable medical device of claim 4, wherein the oscillator is a first oscillator and the resonator is a first resonator having a first center frequency;
   the allocated band of the plurality of communication channels comprises a first plurality of communication channels in a first band and a second plurality of communication channels in a second band different than the first band;
   the receiver further comprising:
   a second oscillator; and
   a second resonator coupled to the second oscillator;
   the receiver being enabled to receive on all of the first plurality of communication channels and all of the second plurality of communication channels simultaneously by applying the quench signal to the first oscillator and the second oscillator.

8. The implantable medical device of claim 1, wherein the receiver is configured to periodically power up to simultaneously receive on all of the plurality of communication channels to detect a wake-up signal and, in response to detecting the wake-up signal, the receiver is configured to select the channel of the plurality of channels for communicating.

9. The implantable medical device of claim 8, wherein the receiver comprises an adjustable channel filter, the receiver configured to adjust the adjustable channel filter to individually pass each channel signal of the plurality of channels in response to detecting the wake up signal and measure a signal energy for each individual channel of the plurality of channels to identify the channel to be selected for communication.

10. The implantable medical device of claim 8, wherein the signal source is configured to adjust the frequency of the quench signal applied to the oscillator to individually pass each channel signal of the plurality of channels in response to detecting the wake up signal and the receiver is configured to measure a signal energy for each individual channel of the plurality of channels to identify the channel to be selected for communication.

11. The implantable medical device of claim 8, wherein the receiver further comprises a memory storing a channel code,
   the receiver identifying an intended communication channel in response to comparing a channel selection signal to the channel code,
   the receiver selecting the channel for communicating as the identified communication channel.

12. The implantable medical device of claim 11, wherein selecting the channel for communicating comprises adjusting the quench signal.

13. The implantable medical device of claim 11, wherein the receiver further comprises an adjustable filter, wherein selecting the channel for communicating comprises adjusting the adjustable filter.

14. A method of operating a receiver configured to receive communication signals on an allocated band of a plurality of communication channels separated in frequency by a channel spacing, the method comprising:
    generating a quench signal having a frequency corresponding to the channel spacing; and
    applying the quench signal to an oscillator of the receiver to enable the receiver to receive communication signals in the allocated band to receive on all of the plurality of communication channels simultaneously.

15. The method of claim 14, further comprising applying the quench signal to at least one other component of the receiver.

16. The method of claim 15, wherein applying the quench signal to at least one other component of the receiver comprises applying the quench signal to at least one of a detector configured to demodulate the received communication signals, an amplifier configured to amplify the received communication signals, or both the detector and the amplifier.

17. The method of claim 14, wherein the allocated band of the plurality of communication channels comprises a first plurality of communication channels in a first band and a second plurality of communication channels in a second band different than the first band;
    wherein applying the quench signal to an oscillator comprises applying the quench signal to a first oscillator associated with receiving communications in the first band;
    the method further comprising applying the quench signal to a second oscillator associated with receiving communications in the second band such that the receiver is enabled to receive communications on all of the first plurality of communication channels in the first band and all of the second plurality of communication channels in the second band simultaneously.

18. The method of claim 14, further comprising coupling a resonator having a resonance frequency to the oscillator to control the oscillation frequency of the oscillator.

19. The method of claim 18, wherein the resonator has a resonance frequency bandwidth corresponding to a frequency bandwidth of one of the plurality of communication channels in the allocated band.

20. The method of claim 18, wherein the resonator is a first resonator having a first center frequency and the allocated band of the plurality of communication channels comprises a first plurality of communication channels in a first band and a second plurality of communication channels in a second band different than the first band, the method further comprising:
    coupling a second resonator to the oscillator, the second resonator having a second center frequency different than the first center frequency; and
    applying the quench signal to the oscillator to enable the received to receive on all of the first plurality of communication channels in the first band and all of the second plurality of communication channels in the second band simultaneously.

21. The method of claim 14, further comprising periodically powering up the receiver to simultaneously receive on all of the plurality of communication channels to detect a wake-up signal; and
    in response to detecting the wake-up signal, selecting the channel of the plurality of channels for communicating.

22. The method of claim 21, wherein further comprising:
    adjusting a channel filter to individually pass each channel signal of the plurality of channels in response to detecting the wake up signal; and
    measuring a signal energy for each individual channel of the plurality of channels to identify the channel to be selected for communication with the transmitter.

23. The method of claim 21, further comprising:
    adjusting the frequency of the quench signal applied to the oscillator to individually pass each channel signal of the plurality of channels in response to detecting the wake up signal; and
    measuring a signal energy for each individual channel of the plurality of channels to identify the channel to be selected for communication with the transmitter.

24. The method of claim 21, further comprising
    comparing a received channel selection signal with a channel code;
    identifying an intended communication channel in response based on the comparison,
    selecting the intended communication channel for communicating.

25. The method of claim 24, wherein selecting the intended communication channel for communicating comprises adjusting the quench signal to adjust the receiver to the intended communication channel.

26. The method of claim 24, wherein selecting the intended communication channel for communicating comprises adjusting an adjustable filter to select the channel for communicating.

* * * * *